United States Patent [19]

Takagawa et al.

[11] Patent Number: 4,978,777
[45] Date of Patent: Dec. 18, 1990

[54] POLYMERIZABLE VINYL MONOMERS AND VINYL RESINS PREPARED THEREFROM

[76] Inventors: Ryozo Takagawa, Toyonaka, Hisaki Yawata, Koji Asakura, Mitsouo Yamada, both of Suita, Hiroharu Ohsugi, Hirakata, Ryuzo Mizuguchi, Yawata, Yoshio Eguchi, Ikeda, all of Japan

[21] Appl. No.: 180,072

[22] Filed: Apr. 11, 1988

[73] Assignee: Nippon Paint Co., LTD, Japan

[30] Foreign Application Priority Data

Apr. 10, 1987 [JP] Japan .................................. 62-089316
Oct. 12, 1987 [JP] Japan .................................. 62-256487

[51] Int. Cl.$^5$ ............................................. C07C 69/52
[52] U.S. Cl. ..................................... 560/224; 526/320
[58] Field of Search ........................................ 520/224

[56] References Cited

U.S. PATENT DOCUMENTS 3,594,410 7/1971 Cohen et al. ...................... 560/224

FOREIGN PATENT DOCUMENTS

GP41871 12/1981 European Pat. Off. .

Primary Examiner—Paul J. Killos
Attorney, Agent, or Firm—Wenderoth, Lind & Ponack

[57] ABSTRACT

A polymerizable vinyl monomer represented by the formula:

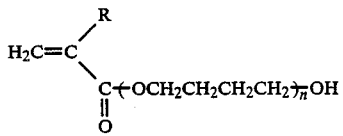

wherein R represents a hydrogen atom or methyl group and n is a real number of 3 to 100, and preparation thereof. The vinyl monomer is useful for the preparation of vinyl resin which is highly reactive in crosslinking with a hardener and capable of resulting in a coating of resilient, tough and flexible nature.

3 Claims, No Drawings

POLYMERIZABLE VINYL MONOMERS AND VINYL RESINS PREPARED THEREFROM

FIELD OF INVENTION

The present invention relates to a novel class of polymerizable vinyl monomers having oxytetramethylene repeating units and preparation thereof. The invention also concerns novel vinyl resin compositions prepared by using the abovementioned vinyl monomers, which are useful, among others, as resinous vehicles in coating compositions.

BACKGROUND OF THE INVENTION

As a measure for utilizing the characteristics of the oxytetramethylene structure such as weather resistance, low viscosity and the like, various attempts have been made to polymerize tetrahydrofuran by ring-opening to obtain a product having functional groups at the end portions thereof.

For example, a number of polyoxytetramethylene glycols having hydroxyl groups at both ends of polyoxytetramethylene chains and having various molecular weights have been prepared by the ring-opening polymerization of tetrahydrofuran and, marketed as raw materials for polyurethane resins. Also, Matveeva et al have reported in Inst. Chem. Phys. Moscow, 1974, 21(3), 191–3, tetramethylene glycol dimethacrylate having at both ends of the tetramethylene chain, polymerizable double bonds, which is useful as a crosslinking monomer, and P. Rempp et al have reported in Polymer Bull. 3, 83–89, 1980, a class of compounds having a considerable number of oxytetramethylene repeating units and a polymerizable vinyl group at only one end portion thereof.

In an acrylic resin to be used as a resinous vehicle in the paint industry, it is often required, from the standpoint of reaction with a hardener such as aminoplast resin, isocyanate compound and the like, and the reaction with a compound having a carboxyl, amino or epoxy group, to incorporate hydroxyl groups into said acrylic resin. The latter is known as a hardening type acrylic resin.

For this end, it is highly desired that a polymerizable vinyl group is located at one end of the oxytetramethylene chain and a hydroxyl group at the other end thereof. In U.S. Pat. No. 4,264,705, there is disclosure of a compound having oxytetramethylene repeating units and having both polymerizable double bond and hydroxyl group at the respective end portions. However, since the said oxytetramethylene unit number (n) is only 2, the desired characteristics such as low viscosity, high resilience and the like cannot be expected with the resulted resin even when used as a constituting material thereof.

It is, therefore, an object of the invention to provide a novel class of polymerizable monomers having a number of oxytetramethylene repeating units and having a polymerizable double bond at one end and hydroxyl group at the other end of the polyoxytetramethylene chain, which can be advantageously prepared in a higher reaction yield in an industrial scale of production and can be used as reactive monomer in the preparation of a novel vinyl resin having a flexible polyoxytetramethylene structure in it.

An additional object of the invention is to provide such vinyl resin composition which is highly reactive in crosslinking with a hardener, of comparatively lower viscosity nature, and capable of resulting in a highly resilient, tough, and flexible coating.

SUMMARY OF THE INVENTION

According to the invention, the aforesaid objects can be attained with a polymerizable vinyl monomer represented by the formula:

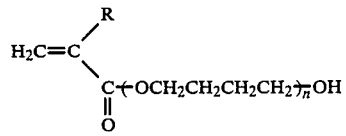

wherein R represents a hydrogen atom or methyl group, and n is a real number of from 3 to 100, and a vinyl resin composition prepared by the polymerization of 20 to 100 mole % of at least one polymerizable vinyl monomer represented by the abovesaid formula, and 80 to 0 mole % of at least one $\alpha,\beta$-ethylenically unsaturated compound other than said vinyl monomer, the resin having a number average molecular weight of 1000 to 100,000.

PREFERRED EMBODIMENTS OF THE INVENTION

The present vinyl monomers are novel compounds, which can be advantageously prepared by either one of the following methods.

That is, in one method, tetrahydrofuran is subjected to ring-opening polymerization in the presence of acrylic or methacrylic acid halide and metallic salt of Lewis acid, and the polymerization is terminated by adding water, aqueous alkali solution or quaternary ammonium base.

In this method, as the acrylic or methacrylic acid halides, such members as acrylic acid chloride, methacrylic acid chloride, acrylic acid bromide, methacrylic acid bromide and the like are preferably used. Preferable examples of metallic salts of Lewis acids are silver salt of antimony hexafluoride, silver tetrafluoroborate, silver perchlorate and the like.

The reaction may be carried out in a conventional way as, for example, by dropwise adding the required amounts of tetrahydrofuran to a solution containing both acrylic or methacrylic acid halide and metalic salt of Lewis acid and stirring the combined mixture under heating.

At the stage when the desired polymerization degree of oxytetramethylene chain is obtained, the reaction is stopped by adding to the reaction system either water, aqueous alkali solution or quaternary ammonium base. As the aqueous alkali solution, any of aqueous solutions of sodium hydroxide, potassium hydroxide, lithium hydroxide and calcium hydroxide may be satisfactorily used. Examples of quarternary ammonium base are tetramethyl ammonium hydroxide, tetraethyl ammonium hydroxide and the like.

If desired, an appropriate non-reactive solvent such as dichloromethane may be used in said reaction.

The present vinyl monomer may also be prepared by polymerizing tetrahydrofuran through ring-opening in the presence of Bronsted acid and terminating the polymerization by metallic salt of acrylic acid, metallic salt of methacrylic acid, amine salt of acrylic acid or amine salt of methacrylic acid.

As the Bronsted acid, mention is made of trifluoromethane sulfonic aicd, trichloro-methane sulfonic acid, perchloric acid, hydrofluoric acid, sulfuric acid, chlorosulfonic acid, fluorosulfonic acid and the like.

If desired, said Bronsted acid may be used in combination with Lewis acid such as antimony pentafluoride.

Examples of metallic salts of acrylic or methacrylic acid are sodium, potassium, lithium, magnesium, calcium, barium and strontium salts of acrylic or methacrylic acid, and examples of amine salts of acrylic or methacrylic acid are ammonium salts of acrylic or methacrylic acid.

The reaction may be carried out in the same way as stated previously in connection with the first method.

Since the abovementioned processes each includes the step of ring-opening polymerization of tetrahydrofuran, the formed product is a mixture of various vinyl monomers whose oxytetramethylene repeating unit numbers (n) differ from each other within a certain range.

If desired, a particular vinyl monomer with a defined repeating unit number may be separated from the thus obtained product by a conventional means such as distillation or the like.

However, for the preparation of vinyl resin composition for coating vehicle use, such separation and purification are almost meaningless and hence the mixed product may be advantageously used as it is.

In that sense, the oxytetramethylene repeating unit number (n) should preferably be taken as an average number of said repeating units, and in this invention, it is expressed in terms of a real number of 3 to 100.

The inventors have found that when the said number is less than 3, the desired flexibility can hardly be obtained in the formed vinyl resin. It is also found that the present monomers will change from liquid to solid state and lose solubility with an increase in said n number and therefore, the maximum number will be about 100 from a practical point of view. Preferably, said number should be in a range of from 3 to 50.

As already stated, since the present monomer is characterized by having a flexible oxytetramethylene chain, one end of which is bound to an addition-polymerizable vinyl group and the other end to a reactive hydroxyl group, it is specifically useful as a reactive monomer for the preparation of heat curing type vinyl resin.

Since the present monomers do possess a both hydrophilic hydroxyl group and hydrophobic oxytetramethylene chain, they can exhibit excellent surface-activation properties and hence, they are useful, in an emulsion polymerization of $\alpha,\beta$-ethylenically unsaturated monomers, as an internal emulsifier.

Thus, in the second aspect of the invention, there is provided a vinyl resin composition prepared by the polymerization of said vinyl monomer and optional other monomers, which is specifically useful as a resinous vehicle for a heat curing type, coating composition.

The present vinyl monomer of the formula:

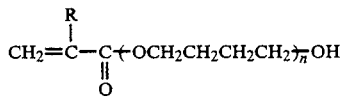

wherein R and n are as defined above, may be used in a range of 20 to 100 mole % of the total monomers to be polymerized. The remaining polymerization monomers may be any of the known $\alpha,\beta$-ethylenically unsaturated compounds customarily used for the preparation of vinyl resin. They are typically classified in the following groups.

(1) carboxyl group containing monomer such as, for example, acrylic acid, methacrylic acid, crotonic acid, itaconic acid, maleic acid, fumaric acid and the like, (2) hydroxyl group containing monomer such as, for example, 2-hydroxyethyl acrylate, hydroxypropyl acrylate, 2-hydroxyethyl methacrylate, hydroxypropyl methacrylate, hydroxybutyl acrylate, hydroxybutyl methacrylate, allyl alcohol, methallyl alcohol and the like, (3) nitrogen containing alkyl acrylate or methacrylate such as, for example, dimethyl aminoethyl acrylate, dimethyl aminoethyl methacrylate and the like, (4) polymerizable amide amide as, for example, acryl amide, methacryl amide and the like, (5) polymerizable nitrile such as, for example, acrylonitrile, methacrylonitrile and the like, (6) alkyl acrylate or methacrylate such as, for example, methyl acrylate, methyl methacrylate, ethyl acrylate, n-butyl acrylate, n-butyl methacrylate, 2-ethyl hexyl acrylate and the like, (7) $\alpha$-olefin such as, for example, ethylene, propylene and the like, (8) vinyl compound such as, for example, vinyl acetate, vinyl propionate and the like, (9) styrene compounds and the like.

The polymerization may be carried out by any of emulsion polymerization, solution polymerization, NAD method and the like, and therefore, the present vinyl resin composition can take the form of an aqueous or solvent type coating composition.

In the case of emulsion polymerization, no additional external emulsifier is required, and this is specifically benefical for the improvement of water resistance of the coating prepared from said aqueous type coating composition.

The number average molecular weight of the present vinyl resin is defined in a range of 1000 to 100,000, since the present resin is mainly designed as a resinous vehicle for a coating composition. For a high solid type coating composition, a preferable range of said molecular weight of the resin is from 1000 to 10,000, and more preferably from 1000 to 5000.

Thus obtained vinyl resin composition of this invention is characterized by the desired properties of low viscosity, higher crosslinking reactivity, and capability of resulting in a coating with excellent film properties, and inter alia, rubber like properties.

The invention shall now be more fully explained in the following Examples. Unless otherwise stated, all parts and % are by weight.

EXAMPLE 1

Into a 300 ml well-dried flask, were placed 153 g of tetrahydrofuran (hereinafter abreviated as THF) freshly distilled after having been saturated with a purified nitrogen gas whose moisture content is less than 1 ppm, and 8.2 g of silver antimony hexafluoride under moisture-cut conditions, and the mixture was, while stirring, allowed to cool to 0° C. Thereafter, 2.5 g of methacrylic acid chloride dissolved in 20 g of THF were added and reacted for 5 minutes. Next, 10 ml of 2N aqueous sodium hydroxide solution were added to stop the reaction. After completion of said reaction, the content was taken in a 500 ml separatory funnel, added with 100 ml of ether and 100 ml of deionized water, vigorously shaken, allowed to stand and the separated aqueous layer was removed off.

The organic layer was washed with water several times and then dried with sodium sulfuric anhydride.

From this layer, ether solvent was removed off under reduced pressure at 20° C. to obtain 19.3 g of clear viscous liquid having aviscosity of 270 cps.

The product was analyzed by IR and $^1$H-MNR, and the following were obtained.

| IR | |
|---|---|
| 3500 cm$^{-1}$ | —OH |
| 2900 cm$^{-1}$ | —CH$_2$— |
| 1720 cm$^{-1}$ | C=O |
| 1640 cm$^{-1}$ | C=C |
| 1120 cm$^{-1}$ | C—O—C |

$^1$H-NMR $$\begin{array}{c} {}^aH \\ {}^bH \end{array} C=C \begin{array}{c} CH_3{}^c \\ C(=O)(OCH_2-CH_2-CH_2-CH_2)_{\overline{n}}OH \end{array}$$

with labels $d$ (inner CH$_2$ groups) and $e$ (outer positions)

| | δ(ppm) |
|---|---|
| a | } 5.46, 6.01 |
| b | |
| c | 1.92 |
| d | 3.39 |
| e | 1.59 |

A mean degree of polymerization (n) (repeating unit number) of THF calculated from area ratio of a or b to d or e was 22.

EXAMPLE 2

The similar experiment as stated in Example 1 was repeated but the reaction conditions were changed to 10 minutes at −20° C., to obtain 9.7 g of a clear viscous liquid having a viscosity of 110 cps.

The same IR and NMR data as given in Example 1 were obtained. The mean degree of polymerization (n) of THF calculated from NMR data was 10.

EXAMPLE 3

The experiments of Example 1 were repeated, but the reaction conditions were changed to 10 minutes at 0° C., to obtain 35.2 g of a clear viscous liquid having a viscosity of 620 cps. The mean degree of polymerization (n) of THF was found to be 50.

EXAMPLE 4

The experiments of Example 1 were repeated, but the reaction conditions were changed to 15 minutes at 0° C., to obtain 70.3 g of a clear viscous liquid having a viscosity of 1200 cps. The mean degree of polymerization (n) of THF was 90.

EXAMPLE 5

The experiments of Example 1 were repeated, but the reaction conditions were changed to 60 minutes at −40° C. to obtain 4.7 g of clear viscous liquid having a viscosity of 35 cps. The mean degree of polymerization (n) of THF was 3.

EXAMPLE 6

Into a 300 ml well-dried flask, were placed 153 g of tetrahydrofuran freshly distilled after having been saturated with a purified nitrogen gas containing less than 1 ppm moisture, and 8.2 g of silver antimony hexafluoride under moisture-cut conditions, and the mixture was, while stirring, allowed to cool to 0° C. Thereafter, 2.5 g of methacrylic acid chloride dissolved in 20 g of THF were added and reacted for 5 minutes. Next, 50 ml of distilled water were added to terminate the reaction, and thereafter, the reaction product was treated in the same way as stated in Example 1, to obtain 20.4 g of a clear viscous liquid having a viscosity of 276 cps. The mean degree of polymerization (n) of THF was found to be 25.

EXAMPLE 7

Into a 300 ml well-dried flask, were placed 153 g of tetrahydrofuran freshly distilled after having been saturated with a purified nitrogen gas containing less than 1 ppm moisture, and 4.7 g of silver tetrafluoroborate under moisture-cut conditions, and the mixture was, while stirring, allowed to cool to −20° C. Thereafter, 2.5 g of methacrylic acid chloride dissolved in 20 g of THF were added and reacted for 10 minutes.

Next, 50 ml of deionized water were added to terminate the reaction, and thereafter, the reaction product was treated in the same way as stated in Example 1 to obtain 8.5 g of a clear viscous liquid having a viscosity of 115 cps. The mean degree of polymerization (n) of THF was 10.

EXAMPLE 8

Into a 300 ml well-dried flask, were placed 11.5 g of tetrahydrofuran freshly distilled after having been saturated with a purified nitrogen gas containing less than 1 ppm moisture and allowed to cool to 0° C. While continuing stirring and cooling, 12.0 g of trifluoromethane sulfonic acid were added and reacted, and at the stage when exothermic reaction was ceased, 46.1 g of distilled THF were again added and reacted.

After 15 minutes, the mixture was added to a dispersion of 40 g of sodium methacrylate in distilled THF and the combined mixture was stirred vigorously to terminate the polymerization reaction. Thereafter, the reaction mixture was treated in the same way as in Example 1 to obtain 11.3 g of a clear viscous liquid having a viscosity of 290 cps. The mean degree of polymerization (n) of THF was 28.

EXAMPLE 9

The same procedures as stated in Example 8 were repeated, but the reaction conditions were changed to 40 minutes at 0° C., to obtain 20.7 g of a clear viscous liquid having a viscosity of 610 cps. The mean degree of polymerization (n) of THF was 51.

EXAMPLE 10

Into a 300 ml well-dried flask, were placed 17.3 g of THF freshly distileed after having been saturated with a purified nitrogen gas containing less than 1 ppm moisture, 92 g of dichloromethane and 8.2 g of silver antimony hexafluoride while cutting moisture and the mixture was stirred and maintained at 20° C. A solution of 2.5 g of methacrylic acid chloride in 10 g of dichloromethane was added and reacted for 20 minutes. Thereafter, the polymerization was stopped by adding 50 ml of deionized water to the reaction system and the reaction mixture was treated in the same way as stated in Example 1 to obtain 8.7 g of a clear viscous liquid having a viscosity of 136 cps. The means degree of polymerization (n) of THF was 13.

EXAMPLES 11 to 14

Similar experiments as stated in Example 1 were repeated, but in these Examples, the reaction consistions were varied and monomers a-1 to a-4 were obtained by shown in the following Table.

| Example | Reaction conditions | | monomer | mean degree of polymerization |
|---|---|---|---|---|
| 11 | −40° C. | 60 min. | a-1 | 3 |
| 12 | −40° C. | 180 min. | a-2 | 6 |
| 13 | −20° C. | 10 min. | a-3 | 10 |
| 14 | 0° C. | 10 min. | a-4 | 45 |

EXAMPLE 15

Into a reaction vessel fitted with a stirrer a thermoneter, a reflux condenser, a nitrogen gas inlet tube and a dropping funnel, were placed 80 parts of Solvesso 100 (trademark, aromatic solvent, manufactured by Shell Petroleum (and 10 parts of xylene and the mixture was heated, while introducing a nitrogen gas, to 130° C. To this, the following mixture was added dropwise in 3 hours at a constant speed.

| Mixture A | |
|---|---|
| monomer a-1 | 60 parts |
| methyl methacrylate | 40 parts |
| t-butyl peroxy-2-ethyl hexanoate | 3 parts |

After completion of said addition, the combined mixture was maintained at the same temperature for 30 minutes.

Thereafter, a mixture of 0.5 part of t-butyl peroxy-2-ethyl hexanoate and 10 parts of xylene was dropwise added at a constant speed in 30 minutes, and the combined mixture was aged at 130° C. for 1 hour and then allowed to cool. A part of the solvent was removed off by distillation to obtain a resinous solution A-1 of the desired solid content. The characteristics of thus obtained resinous solution and of the resin contained were shown in Table 2.

EXAMPLES 16 TO 27 AND COMPARATIVE EXAMPLES 1 TO 3

Similar experiments as stated in Example 15 were repeated excepting substituting the materials and the reaction conditions shown in Table 1 for the materials and conditions given in Example 15. The characteristics of thus obtained resinous solutions and of the resins are shown in Table 2.

EXAMPLES 28 TO 40 AND COMPARATIVE EXAMPLES 4 TO 6

Each of the resinous solutions A-1 to A-13 and B-1 to B-3 obtained in Examples 15 to 27 and Comparative Examples 1 to 3 was added with U-van 20N-60 (melamine resin, trademark of Mitui Tohatsu) in a solid weight ratio of 70/30, and then with a dodecyl benzene sulfonic acid solution (2 wt % of the resin solid), and the combined mixture was well stirred to obtain a coating composition, respectively.

Thus obtained composition was then applied by means of barcoater on a tin plate and baked at 140° C. for 30 minutes. After leaving at a room temperature, the coated plate was subjected to a rubbing test with xylene and with methyl ethyl ketone. The test results are shown in Table 3. Separately, the formed film was removed from the tin plate and subjected to an elongation test with a tensilometer (manufactured by Tohyo Baldwine Co.)

The test results are shown in Table 4.

TABLE 1

| Example | 15 | 16 | 17 | 18 | 19 | 20 | 21 | 22 | 23 | 24 | 25 | 26 | 27 | | | |
|---|---|---|---|---|---|---|---|---|---|---|---|---|---|---|---|---|
| Comparative Example | | | | | | | | | | | | | | 1 | 2 | 3 |
| Resinous solution | A-1 | A-2 | A-3 | A-4 | A-5 | A-6 | A-7 | A-8 | A-9 | A-10 | A-11 | A-12 | A-13 | B-1 | B-2 | B-3 |
| Monomers | | | | | | | | | | | | | | | | |
| monomer a-1 | 60 | 60 | 80 | | | | | | | | | | | | | |
| monomer a-2 | | | | 100 | 60 | 60 | 60 | 80 | | | | | | | | |
| monomer a-3 | | | | | | | | | 100 | 70 | 70 | 80 | | | | |
| monomer a-4 | | | | | | | | | | | | | 90 | | | |
| methyl methacrylate | 40 | 20 | 20 | | 40 | 21 | 21 | 20 | | 30 | 15 | 20 | 10 | 40 | 47 | 34 |
| n-butyl acrylate | | 20 | | | | 19 | | | | | | | | 40 | | |
| ethyl methacrylate | | | | | | | 19 | | | | | | | | | |
| 2-ethyl hexyl acrylate | | | | | | | | | | | 15 | | | | | |
| 2-hydroxyethyl methacrylate | | | | | | | | | | | | | | 20 | | |
| Placcel FA-3 (Note 1) | | | | | | | | | | | | | | | 53 | |
| Placcel FM-5 (Note 2) | | | | | | | | | | | | | | | | 66 |
| Initiator | | | | | | | | | | | | | | | | |
| t-butyl peroxy-2-ethyl hexanoate | 3 | 3 | 3 | 5.5 | 5.5 | 5.5 | 5.5 | 3.0 | 5.5 | 5.5 | 5.5 | 5.5 | 1.0 | 5.5 | 5.5 | 5.5 |
| Solvent | | | | | | | | | | | | | | | | |
| Solvesso 100 | 80 | 80 | 80 | 100 | 100 | 100 | 100 | 100 | 100 | 100 | 100 | 100 | 80 | 100 | 100 | 100 |
| xylene | 20 | 20 | 20 | — | — | — | — | — | — | — | — | — | 20 | — | — | — |
| Polymerization temperature (°C.) | 130 | 130 | 130 | 150 | 150 | 150 | 150 | 130 | 150 | 150 | 150 | 150 | 130 | 150 | 150 | 150 |
| mole % of monomer a | 34.4 | 34.4 | 61.5 | 100 | 23.0 | 25.8 | 24.1 | 44.4 | 100 | 22.8 | 33.6 | 25.8 | 21.3 | — | — | — |

Note 1
Caprolactone type monomer, trademark of Daisel K.K.
Note 2
Caprolactone type monomer, trademark of Daisel K.K.

TABLE 2

| Resinous solution | A-1 | A-2 | A-3 | A-4 |
|---|---|---|---|---|
| molecular weight (Note 3) | 3000 | 3400 | 3800 | 1800 |
| Solid content (%) | 90 | 90 | 90 | 90 |
| viscosity (Note 4) | $Z_1$-$Z_2$ | $Z_1$ | $Z_1$ | V-W |

TABLE 2-continued

| Resinous solution | A-5 | A-6 | A-7 | A-8 |
|---|---|---|---|---|
| molecular weight (Note 3) | 2000 | 2200 | 2100 | 4500 |
| Solid content (%) | 90 | 90 | 90 | 90 |
| viscosity (Note 4) | V | U-V | U-V | U-V |
| Resinous solution | A-9 | A-10 | A-11 | A-12 |
| molecular weight (Note 3) | 2200 | 2600 | 2900 | 2700 |
| Solid content (%) | 90 | 90 | 90 | 90 |
| viscosity (Note 4) | U | T-U | T | T-U |
| Resinous solution | A-13 | B-1 | B-2 | B-3 |
| molecular weight (Note 3) | 9200 | 1900 | 2000 | 2100 |
| Solid content (%) | 90 | 70 | 85 | 85 |
| viscosity (Note 4) | Y-Z | V-W | $Z_4$-$Z_5$ | $Z_4$-$Z_5$ |

Note 3
number average molecular weight determined by Gel permeation chromatography
Note 4
bubble viscometer (25° C.)

TABLE 3

| Example | 28 | 29 | 30 | 31 | 32 | 33 | 34 |
|---|---|---|---|---|---|---|---|
| Resinous solution | A-1 | A-2 | A-3 | A-4 | A-5 | A-6 | A-7 |
| xylene rubbing test (Note 5) | | | | | | | |
| methyl ethyl ketone rubbing test | | | | | | | |

| Example | 35 | 36 | 37 | 38 | 39 | 40 |
|---|---|---|---|---|---|---|
| Resinous solution | A-8 | A-9 | A-10 | A-11 | A-12 | A-13 |
| xylene rubbing test (Note 5) | | | | | | |
| methyl ethyl ketone rubbing test | | | | | | |

| Comparative Example | 4 | 5 | 6 |
|---|---|---|---|
| Resinous solution | B-1 | B-2 | B-3 |
| xylene rubbing test (Note 5) | X | ~Δ | ~Δ |
| methyl ethyl ketone rubbing test | X | ~Δ | ~Δ |

Note 5
After 50 times reciprocating rubbing motion, film appearance was observed by the naked eye.
 no change
Δ slight white blooming
X blooming

TABLE 4

| Example | 28 | 29 | 30 | 31 | 32 |
|---|---|---|---|---|---|
| Resinous solution | A-1 | A-2 | A-3 | A-4 | A-5 |
| film thickness (μ) | 72 | 73 | 72 | 70 | 75 |
| elongation (%) at 20° C. | 82 | 85 | 94 | 110 | 103 |

| Example | 33 | 34 | 35 | 36 | 37 |
|---|---|---|---|---|---|
| Resinous solution | A-6 | A-7 | A-8 | A-9 | A-10 |
| film thickness (μ) | 75 | 76 | 74 | 72 | 73 |
| elongation (%) at 20° C. | 107 | 112 | 100 | 120 | 118 |

| Example | 38 | 39 | 40 |
|---|---|---|---|
| Resinous solution | A-11 | A-12 | A-13 |
| film thickness (μ) | 73 | 70 | 72 |
| elongation (%) at 20° C. | 124 | 120 | 135 |

TABLE 4-continued

| Comparative Example | 4 | 5 | 6 |
|---|---|---|---|
| Resinous solution | B-1 | B-2 | B-3 |
| film thickness (μ) | 74 | 75 | 74 |
| elongation (%) at 20° C. | 15 | 40 | 50 |

What is claimed is:

1. A polymerizable vinyl monomer represented by the formula:

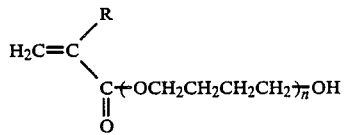

wherein R represents a hydrogen atom or methyl group; and n is a real number of from 3 to 100.

2. A process for preparing a polymerizable vinyl monomer of the formula:

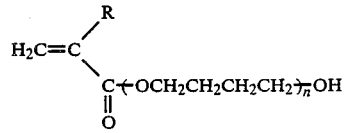

wherein R represents a hydrogen atom or methyl group; and n is a real number of from 3 to 100, comprising subjecting tetrahydrofuran to a ring opening polymerization in the presence of acrylic or methacrylic acid halide and metallic salt of Lewis acid, and terminating the polymerization with water, aqueous alkali solution or quaternary ammonium base.

3. A process for preparing a polymerizable vinyl monomer of the formula:

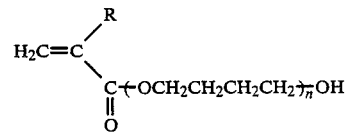

wherein R represents a hydrogen atom or methyl group; and n is a real number of from 3 to 100, comprising subjecting tetrahydrofuran to a ring opening polymerization in the presence of Bronsted acid and terminating the polymerization with a member selected from the group consisting of metallic salt of acrylic acid, metallic salt of methacrylic acid, amine salt of acrylic acid and amine salt of methacrylic acid.

* * * * *